United States Patent [19]

Kido et al.

[11] Patent Number: 5,003,571
[45] Date of Patent: Mar. 26, 1991

[54] X-RAY IMAGE EQUIPMENT

[75] Inventors: Cyouichiro Kido, Aichi; Katsuhei Hotta, Tajimi; Takuya Haneda, Hachiouji, all of Japan

[73] Assignee: Nippon Identograph Co., Ltd., Japan

[21] Appl. No.: 532,222

[22] Filed: Jun. 1, 1990

Related U.S. Application Data

[63] Continuation of Ser. No. 244,346, Sep. 14, 1988, abandoned.

[30] Foreign Application Priority Data

Sep. 2, 1987 [JP] Japan ................................. 62-234918

[51] Int. Cl.⁵ .............................................. G03B 42/02
[52] U.S. Cl. ........................................ 378/99; 378/37; 358/111
[58] Field of Search ...................... 378/99.37; 358/111

[56] References Cited

U.S. PATENT DOCUMENTS

| | | | |
|---|---|---|---|
| 3,854,049 | 12/1974 | Mistretta et al. | 378/99 |
| 4,020,347 | 4/1977 | Geluk | 358/111 |
| 4,482,918 | 11/1984 | Keyes et al. | 358/111 |
| 4,541,106 | 9/1985 | Belanger et al. | 358/111 |
| 4,542,459 | 9/1985 | Riederer | 378/99 |
| 4,543,604 | 9/1985 | Grosse | 358/111 |
| 4,558,223 | 12/1985 | Broadhurst et al. | 250/374 |
| 4,611,341 | 9/1986 | Brody | 378/99 |
| 4,710,637 | 12/1987 | Luckey et al. | 378/37 |
| 4,722,097 | 1/1988 | Haendle | 378/99 |
| 4,735,310 | 4/1988 | Goldenberg | 128/654 |
| 4,759,045 | 7/1988 | Lasky | 378/37 |
| 4,813,061 | 3/1989 | Kiakegawa | 358/111 |

FOREIGN PATENT DOCUMENTS 3248646 7/1983 Fed. Rep. of Germany ...... 358/111

Primary Examiner—Constantine Hannaher
Assistant Examiner—David P. Porta
Attorney, Agent, or Firm—Wall and Roehrig

[57] ABSTRACT

Soft x-ray radiation, which has a lower level of radiation, is transmitted to a target (i.e., the breast). The transmitted image of the target is refined through various computerized processes. All data is stored in a multiple image memory or filed in a laser having a large memory capacity. Stored images can be viewed on a TV monitor or recalled and interfaced to a host computer. Accordingly, the present invention is designed for mass-screening. The whole sequence of data acquisition and processing is controlled by an operation controller, which also controls the accelerating voltage of the soft x-ray radiation. The equipment is not limited for use in detecting breast cancer and is equally adapted in examining infants or others who cannot tolerate large or heavy radiation dosages.

5 Claims, 1 Drawing Sheet

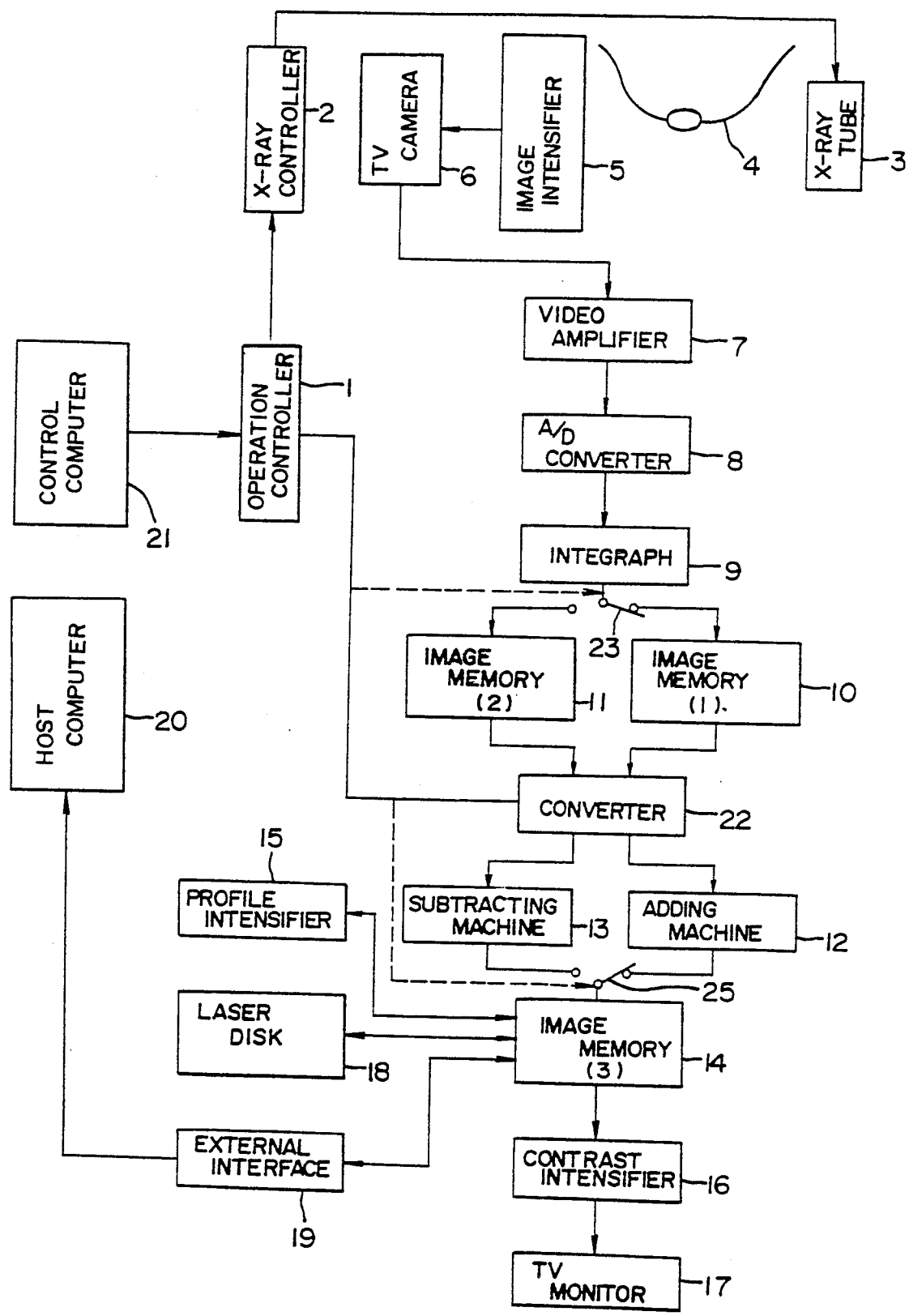

X-RAY IMAGE EQUIPMENT

This is a continuation of co-pending application Ser. No. 244,346 filed on Sept. 14, 1988.

BACKGROUND OF THE INVENTION

This invention relates to x-ray imaging equipment for obtaining transmitted images of soft human tissue, especially from the breast area.

It is generally believed that early detection of cancer is necessary in order to enhance a patient's chances of recovery. It is anticipated that mammary carcinoma (or breast cancer) will soon be ranked at the highest cause of death among females in certain countries. It is therefore necessary to conduct mass-screening of females in these high risk areas so that mammary (or simply breast) cancer can be detected as early as possible.

Although palpation has been the major method for detecting breast cancer, a technique has been developed in which radiation having a high x-ray absorption coefficient on soft tissue such as the breast is used to produce x-ray images on film. However, since the aforementioned soft radiation has high absorption attenuation by breast tissue, the radiation methods pose certain problems. The amount of radiation required to obtain a clear image by a film photographing technique may be relatively high and accordingly, the risk to patients receiving high radiation dosages may be correspondingly high.

In order to reduce the effects of absorption attenuation, radiation at shorter wavelengths, that is, wavelengths shorter than soft x-rays, is used in some radiography processes. This short wavelength radiation however, will penetrate all types of tissues and it is therefore difficult to discern diseased tissue from healthy tissue in an x-ray picture. The term soft x-rays or soft x-ray radiation as herein used shall refer to x-ray radiation that is at wavelengths capable of producing an image in which diseased or cancerous tissue can be defined and at low enough levels where it will not damage healthy tissues during the exposure period.

OBJECTS AND SUMMARY OF THE INVENTION

It is therefore an object of the present invention to detect and examine human tissue by using soft x-rays. The main objects of this invention stem from the practical need to reduce patient radiation dosages and to provide x-ray equipment that can accurately detect changes in breast tissue at these low dosage levels.

In order to pursue the purposes mentioned above, the embodiments and equipment of the invention include (1) x-ray equipment which radiates focused soft x-rays on a target to be detected or examined at relatively low radiation level, (2) a high-speed switching device by which the accelerating voltage for the x-ray tube can be controlled, (3) an image intensifier which functions to convert a transmitted image of the target into a visible image, (4) a video camera by which the visible image is converted to video signals, (5) an integraph by which noise in the video signals is reduced or eliminated, (6) multiple image memories, which can input and output different multiple video signal images obtained through the above mentioned high-speed switching devices, (7) a computer by which video signal images which are previously stored in memory are added or subtracted to enhance the image, (8) a contrast intensifier, which has an intensifying function to contrast the image information which has previously been processed by the noted computer, (9) a profile intensifier, which intensifies outlines of the video signals processed by the computer, (10) a video monitor for viewing the enhanced images from the image memory, (11) a recording device by which the computed image information is stored in a form that can be recalled and a connecting means for connecting the image memory to a host computer.

The significant function of this invention can be explained in accordance with the following description.

Micro-focused soft x-rays having a low radiation level directed at a target to be examined, for instance the breast, by suitable x-ray equipment. The voltage of the x-ray radiation equipment is accelerated in multiple steps of, for example, 25 to 50 kV, by means of a high-speed switching mechanism. As a result, different types of tissue within a single target area are exposed several times to soft x-rays at different accelerating voltages to create several images of the same target.

A transmitted image of the target is converted to a visible image through means of an image intensifier. The visible image is further converted to video signals by a video camera. The video signal is, in the next step, integrated several times by use of an integraph so that random noise in the video signal is greatly reduced or eliminated.

Separate video signal images produced by soft x-ray radiation using different accelerating (energy) voltages, are processed through the integraph in series and are stored in a suitable image memory.

The stored video signals are read out of memory and are subjected to an adding or subtracting operation in a computer to provide a single enhanced image. The signal contrast of the enhanced image is intensified by a contrast intensifier and the profile is also intensified by a profile intensifier. Consequently, the original target image is now both refined and enhanced so as to provide for greater detail and more usable data without the use of heavy radiation dosages.

The above and other objects, features and advantages of this invention will be more fully understood from the detailed description of the invention below, which should be read in connection with the accompanying drawing.

BRIEF DESCRIPTION OF THE DRAWING

The accompanying figure is a schematic block diagram illustrating a construction of an embodiment of this invention which includes an operating controller 1, x-ray controller 2, x-ray tube 3, target to be examined 4, image intensifier 5, video camera 6, integraph 9, image memories 10, 11 and 14, profile intensifier 15, contrast intensifier 16, and video monitor 17 and other associated system components.

DETAILED DESCRIPTION OF PREFERRED EMBODIMENT

The detailed function of the present invention will be explained with reference to the attached schematic block drawing.

In this example, a rotating Mo (molybdenum) anode equipped x-ray tube, having a focus diameter of 100 to 200 (micron meter), is employed. As will be explained below, the system also employs a two-step high-speed switching device for selectively switching the accelerating voltage of the x-ray tube between 26 and 43 kV.

As shown in the attached drawing, a control computer 21 is connected to the operating controller 1 by appropriate lead wires. An x-ray controller 2 is used to connect the operating controller 1 and an x-ray tube 3.

A target to be detected or examined 4 is placed between the focusing lens of x-ray tube 3 and an image intensifier 5 so that the soft x-ray radiation from the x-ray tube 3 passes through the target to produce an image thereof which is transmitted to an image intensifier 5.

The target image is registered on a fluorescent plate in the image intensifier 5 and the image then recorded by a video camera through means of an appropriate lens system (not shown). The video output terminal of the camera is connected to the input terminal of a video amplifier 7. The output terminal of the video amplifier 7, in turn, is connected to input terminal of an analogue to digital (A/D) converter 8, which provides a digital output signal containing the acquired video signal information. The output terminal of the A/D converter 8 is coupled to an input terminal of an integraph 9 wherein the signal data is integrated several times to reduce or eliminate background noise.

The output terminal of the integraph 9 is connected to the input terminal of image memory 10 or 11 by means of an electrically controlled selector switch 23. Image data concerning a target image acquired at 26 kV are stored in one memory while data concerning target image acquired at 43 kV is stored in the other memory. The output terminals of the two memories are both connected through a converter (switch) 22 to the input terminals of the respective adding circuit 12 and subtracting circuit 13 which are housed in a computer.

The output terminal of either the adding circuit 12 or the subtracting circuit 13 is selectively connected through means of a second electrically controller selector switch 25 to the input terminal of the enhanced image memory 14. The output terminal of the enhanced image memory 14 is then connected to the input terminal of the contrast intensifier 16, and the output terminal of the contrast intensifier 16, in turn, is coupled to the input terminal of a video monitor.

The aforementioned enhanced image memory 14 is also connected to a profile intensifier 15, laser disk 18, or external interface 19 by suitable lead wires. The external interface 19 is connected to a host computer 20 by signal leading wires.

In practice, the operating controller 1 controls the switching functions of selector switch 23 so that output of integraph 9 can be coupled to the input terminal of the image memory 10 or image memory 11. The controller 1 also controls the function of selector switch 25 to selectively connect the output of either the adding circuit 12 or the subtracting circuit 13 to the input of the image memory 14. The operating controller 1 further operates the switching function of converter 22 and the changing of the acceleration voltage applied to the x-ray tube.

The x-ray controller 2 and x-ray tube 3 typically are housed together as a single piece of equipment. The operating controller 1 and x-ray controller 2 are electrically coupled to form a high-speed switching network. The circuits adding 12 and subtracting 13 are contained in a minicomputer or the like.

Referring to the aforementioned construction, the operating sequences and functions of this invention are explained below.

When an operator initiates the operating controller 1, the x-ray image equipment is activated according to a program stored in the control computer 21. Upon initiating the operating controller 1, a first switching signal from the x-ray controller 2 is applied to the x-ray tube 3. For example, if the accelerating voltage for the x-ray tube 3 is set at 26 kV, the micro-focus soft x-ray 3 are radiated from x-ray tube 3 at this accelerating voltage. The soft x-rays are radiated at the target 4, such as a human breast, for a predetermined short period of time. The soft x-rays generated by this procedure have different characteristics from those used by ordinary chest-/lung x-ray equipment. The wavelength of this soft radiation is only several angstrom and the radiation dose level is in the range of 30 to 50 milli-roentgens. More conventional x-ray equipment used for chest or lung examination operates at 0.5 to 1.0 angstrom and produce 300 to 800 milli-roentgens. The soft x-rays used in the practice of the present invention thus pose less of a danger to a patient.

The soft x-rays are radiated through the breast, which is supported in a well known manner, from the side face thereof. The breast is placed between x-ray tube 3 and an image intensifier 4. Any inhomogeneity in the amount of radiation attenuation is compensated for by a Be(beryllium) compensating filter (not shown) mounted inside the x-ray tube 3. The radiated soft x-rays passing through the breast are converted to a visible image by the image intensifier 5 and the visible image is further converted to a video signal by video camera 6.

The camera output signal is amplified by a video amplifier 7 and fed into an integraph 9 by means of an A/D converter 8. The video signal supplied to the integraph 9 is integrated several times, resulting in a reduction in the signal random noise level. The quantum noise caused by the random low energy x-rays is reduced to $1/\sqrt{n}$, where n is the repetitive number of the integration operations.

The first video signal image, which has been integration-processed, is stored in the image memory 10 as a stationary image. Upon the completion of the reducing process, a switching command is provided by the operating controller 1 to switch 23 and, at the same time, a second switching signal sent to the x-ray tube 3.

According to the signal sequences described above, the accelerating voltage of the x-ray tube 3 is now set at 43 kV, the micro-focus soft x-rays with the accelerating energy voltage of 43 kV is radiated from the x-ray tube 3 onto the breast for a prescribed period of time.

The radiated soft x-rays with 43 kV is integration-processed, with the same procedures as the aforementioned case of 26 kV, to obtain video signals which are further recorded at the second image memory 11.

In the next step, the image information, which is stored in the image memory 10 and 11, is forwarded to adding circuit 12 and is then added. Through means of the adding operation, it is possible to collect a wide and dynamic range of signals varying from relatively thin target segments such as a soft breast tissue, to the thicker target segments found in the sternum region near the lymph nodes. This video image data is fed through switch 25 to the enhance image memory 14. Switch 25 is cycled on command by operational controller 1. The capacity of the image memory 14 is sufficiently large to prevent overflow problems.

At the same time, information from image memory 10 or 11 can also be subtracted in subtracting circuit 13 by cycling appropriate switching circuits in converter 22.

By performing this subtracting process, images produced by radiation with different penetration coefficients due to different levels of energy are intensified and enhanced.

The information, recorded in the image memory 14, is then fed to the profile intensifier 15, where the input signal is processed to (1) intensify a high frequency component of the image through a differential filter and a high-pass filter and (2) intensify the profile of the object.

The signal at the completion of the processing is stored back in the image memory 14. The stored images can be monitored by the video monitor on demand. Signals which are stored in the image memory 14 are input into contrast intensifier 16 to improve the image contrast over the entire image area before being viewed.

Consequently, images of tissues difficult to diagnose, such as calcificated necrotic tissue for example, can be clearly displayed. At the same time, this image intensification step brings other beneficial effects. Shading can be remarkably improved since this image component, which is not related to energy, can be eliminated by the process. By pursuing the aforementioned signal processing technique, carcinoma tissue can be specifically intensified. If, for example, the equipment possesses the recognition capacity of a component up to 1000 steps and the radiated necrotic tissue shows a contrast of 50 steps, then the intensification processing will convert the 50-step contrast level to 700 to 800. When an entire image is observed under a uni-contrast condition, the necrotic tissue can be resolved at only 50 steps by a conventional method. This invention thus makes it possible to resolve the obtained image into 700 to 800 steps, as mentioned above.

Furthermore, data recorded in the image memory 14 can be memorized on a laser disk 18 as digital signals and read out when needed. Accordingly, a film is not required. For instance, one 5-inch laser disk has a data storage capacity for recording data for about 400 patients'. Therefore, equipment suitable for a mass screening program can be constructed at low costs.

Moreover, automatized examinations can be realized by sending data to a host computer 20 through external interface 19.

In general, there are two types of tumors, which are detected during a breast examination. One is a clot of adipose tissue and the other is calcificated nucleus generated by mammary carcinoma. These two cancers generally cannot be distinguished if they are observed under uni-contrast conditions. However, when the obtained image is contrast-intensified and treated under an energy adding/subtracting process as herein described, the diseased tissue inside the tumor can be clearly recognized. Consequently, an accurate diagnosis can be made whether the tumor is caused by a breast cancer or not.

Such diagnosis is usually made by a doctor's palpation, which requires skill and experience. On the other hand, an accurate diagnosis can be achieved without any requirements of special skill using the apparatus of the present invention.

Although the aforementioned detailed description of the invention concerns detection of breast cancer, this invention is not limited to this embodiment and can be applied to infants or others who cannot be examined by other procedures.

Moreover, although the explained description of embodiments of this invention refers to a two-step high-speed switching mechanism, the embodiment of this invention is not limited to a two-step switching, but it can be modified to construct a switching mechanism for more than a three-step system.

The significant effect of this invention stems from the fact that the transmitted image of the target being detected or examined can be obtained by soft x-rays using an exchangeable accelerating voltage. The transmitted image is converted to an electrical signal, which is subsequently processed by an integraph, computation, profile intensification, and contrast intensification. Therefore, a detailed observation of any changes in tissue in the target area can be easily detected.

Moreover, the image data can be stored in memory and viewed by a monitor. The stored data can also be recorded onto a laser disk. Consequently, expensive films are not required, and mass screening efforts can be achieved economically.

Furthermore, since soft x-rays with a low level of energy can be used, the radiation dose for both operator and patient is remarkably reduced and an automatized examination can also be pursued when the system is interfaced to a host computer.

What is claimed is:

1. Apparatus for providing high quality x-ray images of soft human tissue with a minimum amount of patient exposure that includes, x-ray means that includes a tube for radiating a target with soft radiation of wavelengths that are longer than one angstrom to produce images of said target, switching means associated with the x-ray tube for selectively changing the acceleration voltage applied to said x-ray tube to provide a first set of images produced at a first acceleration voltage and a second set of images produced at a second acceleration voltage, means to render the two sets of image visible, video camera means for recording both sets of images and providing video signals thereof, means for digitizing the video signals, integrating means for acting on the digitized image signal to remove unwanted noise therefrom, a first memory means for storing data relating to the first set of image signals and a second memory means for storing data relating to the second set of image signals, adding means for adding image signal data from said first and second memory means to enhance the dynamic range of said signal data, subtracting means for subtracting image signal data from said first and second memory means to enhance the intensity of said signal data, third memory means for storing the enhanced signal data to said adding and subtracting means, contrast intensifier means connected to said third memory means for increasing the resolution of the enhanced signal data, and video display means for viewing the enhanced signal data.

2. The apparatus of claim 1 that further includes a profile intensifier means connected to said third memory means for intensifying high frequency components of the stored signal data and returning the profile intensified signal data to said third memory.

3. The apparatus of claim 2 that further includes a laser disk means connected to the third memory means to provide further storage of the enhanced signal data.

4. The apparatus of claim 1 that further includes a converter means for forwarding stored signal data from said first and second memory means to said adding and subtracting means.

5. The apparatus of claim 4 that further includes a controller means for controlling the operation of said switching means, said first and second memory means, and said converter means.

* * * * *